(12) United States Patent
Pernot et al.

(10) Patent No.: US 8,118,594 B2
(45) Date of Patent: Feb. 21, 2012

(54) DENTAL HANDPIECE WITH A UNITARY BODY AND AN ELECTRICALLY CONDUCTIVE AND ELASTIC CONNECTION ELEMENT

(75) Inventors: Jacques Pernot, Vieilley (FR); Jean-Claude Boinot, Besancon (FR)

(73) Assignee: Micro-Mega International Manufactures, Besançon (FR)

( * ) Notice: Subject to any disclaimer, the term of this patent is extended or adjusted under 35 U.S.C. 154(b) by 1065 days.

(21) Appl. No.: 10/580,373

(22) PCT Filed: Sep. 23, 2004

(86) PCT No.: PCT/FR2004/002392
§ 371 (c)(1), (2), (4) Date: May 23, 2006

(87) PCT Pub. No.: WO2005/063140
PCT Pub. Date: Jul. 14, 2005

(65) Prior Publication Data
US 2007/0065774 A1 Mar. 22, 2007

(30) Foreign Application Priority Data
Nov. 25, 2003 (FR) .................. 03 13899
Mar. 25, 2004 (FR) .................. 04 03047

(51) Int. Cl.
*A61C 3/00* (2006.01)
*A61C 1/08* (2006.01)

(52) U.S. Cl. .............. 433/27; 433/114; 433/126

(58) Field of Classification Search .......... 433/133, 433/114, 126, 224, 27; 600/590
See application file for complete search history.

(56) References Cited

U.S. PATENT DOCUMENTS

| | | | | |
|---|---|---|---|---|
| 274,008 | A | * | 3/1883 | Lincoln .............. 433/133 |
| 1,292,632 | A | * | 1/1919 | Nemmers ............ 279/76 |
| 2,263,808 | A | * | 11/1941 | Hutchinson ........ 433/104 |
| 4,504,227 | A | * | 3/1985 | Lohn .................... 433/131 |
| 5,011,408 | A | * | 4/1991 | Nakanishi ........... 433/127 |
| 5,575,647 | A | | 11/1996 | Grubbs |
| 5,897,315 | A | | 4/1999 | Matoba et al. |
| 5,902,105 | A | | 5/1999 | Uejima et al. |
| 6,149,430 | A | * | 11/2000 | Nemetz et al. ..... 433/132 |
| 6,227,854 | B1 | * | 5/2001 | Helfenbein et al. .... 433/128 |
| 7,074,041 | B2 | * | 7/2006 | Kuhn ................... 433/127 |
| 2002/0168610 | A1 | | 11/2002 | Papanek et al. |

FOREIGN PATENT DOCUMENTS

| | | |
|---|---|---|
| EP | 0174695 | 3/1986 |
| EP | 0322896 | 7/1989 |
| EP | 0937440 | 8/1999 |
| FR | 799430 | 6/1936 |
| FR | 2393564 | 1/1979 |
| FR | 2863862 | 6/2005 |

* cited by examiner

*Primary Examiner* — John J Wilson
(74) *Attorney, Agent, or Firm* — Gary M. Cohen

(57) ABSTRACT

A dental handpiece (1) includes mechanical components, in particular, a tool-holder assembly for the attachment and for the rotational driving of a dental instrument about a drive axis (6) and an assembly for the transmission of such movement. The mechanical components are mounted in the interior of a body (2) having a head (4) and a handle (3). The mechanical components of the handle and the head of the handpiece are electrically connected by an elastic and electrically conducting connecting device.

32 Claims, 4 Drawing Sheets

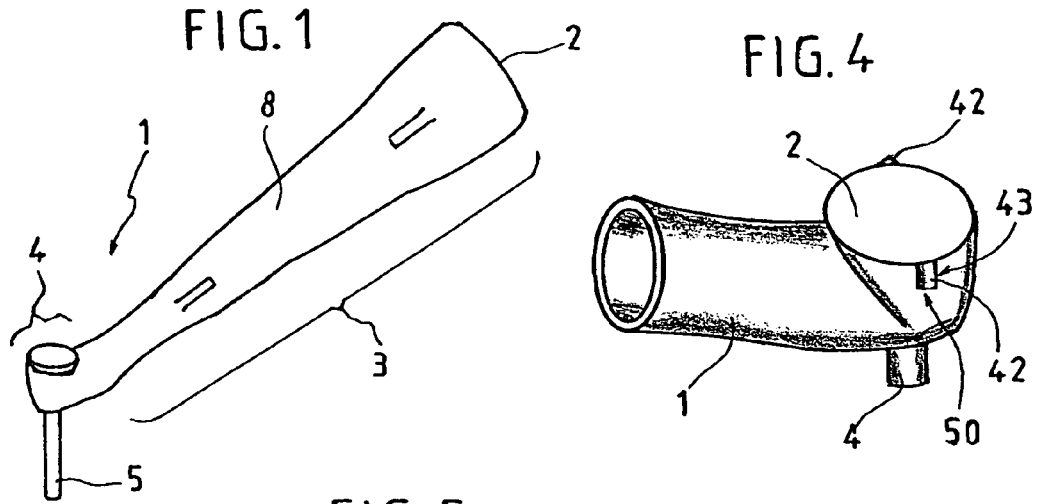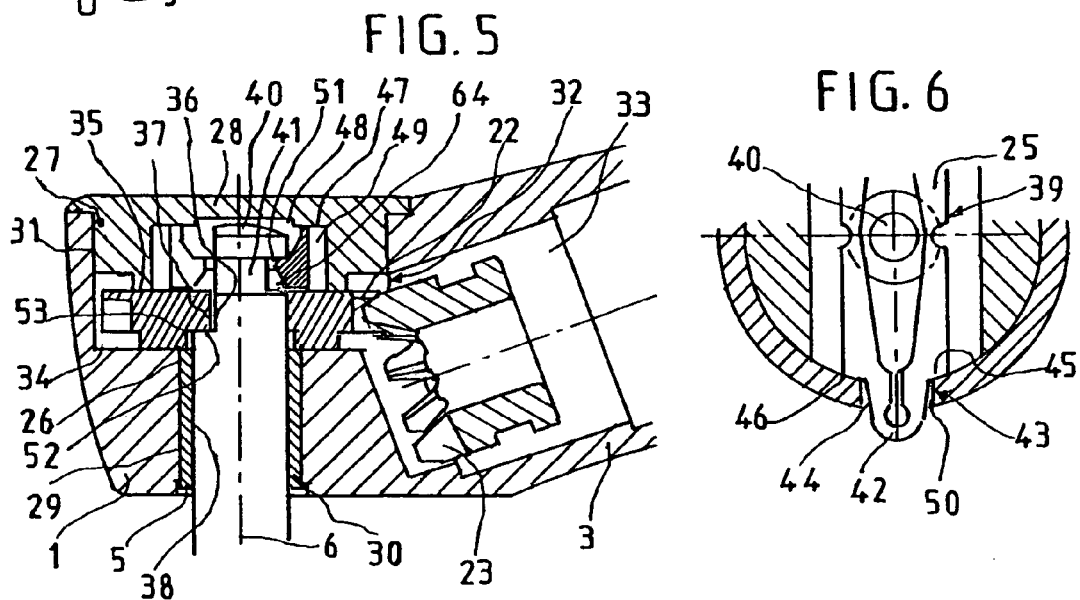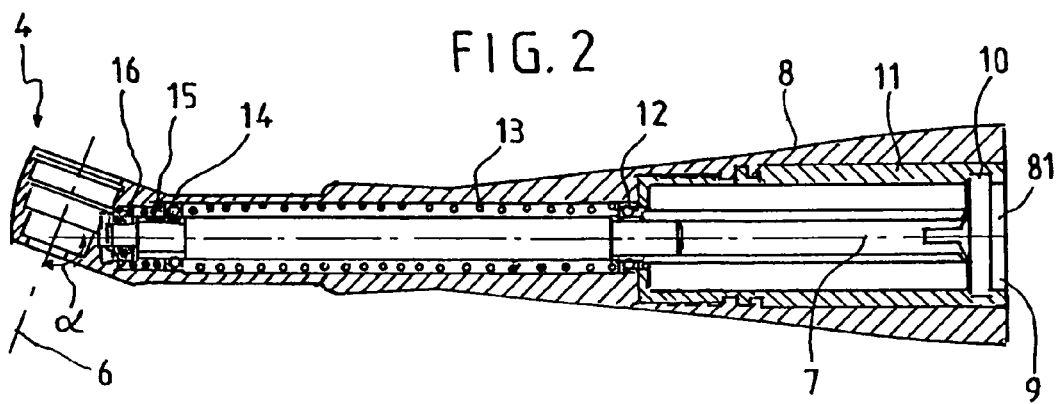

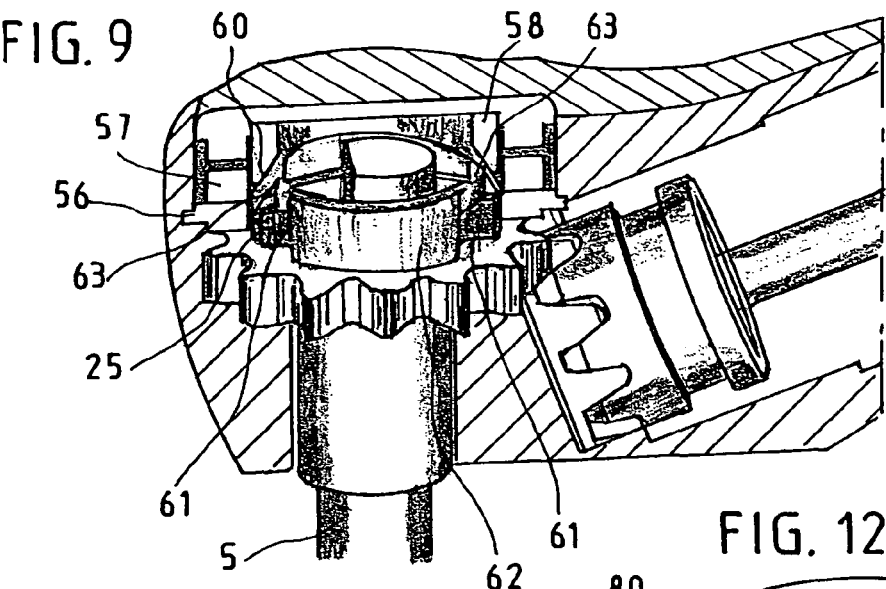
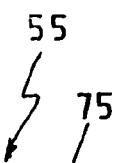
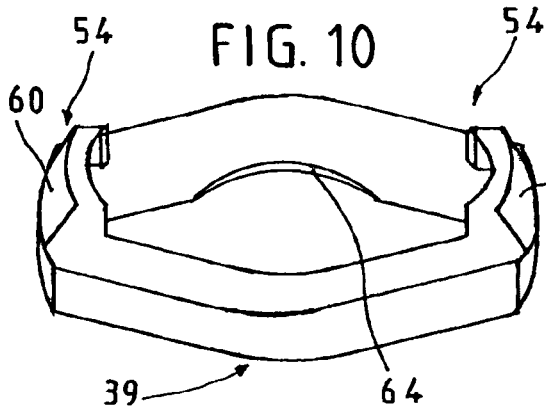
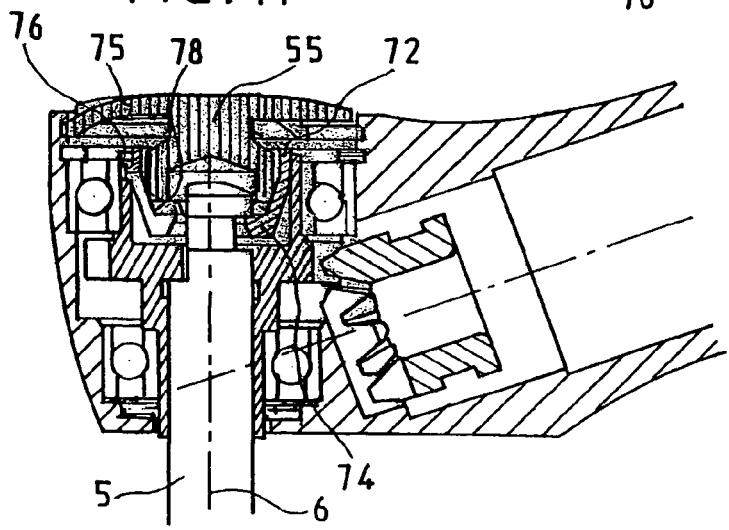
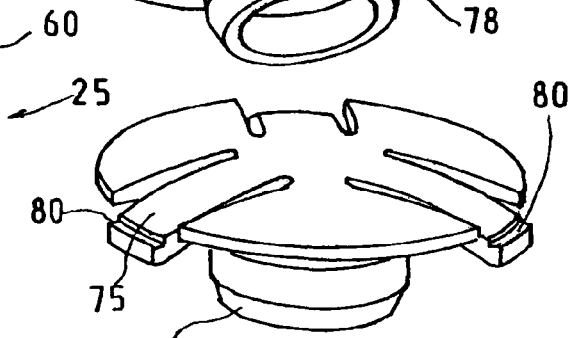

DENTAL HANDPIECE WITH A UNITARY BODY AND AN ELECTRICALLY CONDUCTIVE AND ELASTIC CONNECTION ELEMENT

BACKGROUND OF THE INVENTION

The present invention relates to a novel type of dental handpiece.

Previously disclosed dental handpieces are of two types; straight handpieces and contra-angle handpieces.

In the case of contra-angle handpieces, the body of the handpiece is comprised of a handle exhibiting an elbow and a head. This results in an embodiment which requires at least two parts for the body, and very often three parts, to permit the assembly of the internal components of the handpiece. This also requires a plurality of bearings; at least three in number. It will be appreciated that this type of design does not permit a reduction in costs to any significant degree.

It is, therefore, an object of the present invention to provide a novel structure for handpieces that is capable of replacing the current handpieces, and which permits the production of the body in a single piece, whether for handpieces that are driven by mechanical means or for handpieces that are driven by an air turbine.

SUMMARY OF THE INVENTION

This object is achieved in accordance with the present invention by providing a dental handpiece of a type comprised of mechanical components, in particular a tool-holder assembly for the attachment and for the rotational driving of a dental instrument about a drive axis, and an assembly for the transmission of desired movement. The mechanical components are mounted in the interior of a body having a head and a handle. The body is formed from a single piece, forming an envelope. One part of the body serves as a handle, and the other part of the body constitutes a head. The head includes a first housing which opens out, with at least one opening dimensioned to permit introduction of the component parts of the head and their assembly in the interior of the body. The handle includes a second longitudinal housing having a rectilinear axis which, on the one hand, opens out at the extremity of the handle via an opening and which, on the other hand, opens out in the first housing via a lateral opening. The opening at the extremity of the handle is dimensioned to permit introduction of the internal component parts of the handle, and their assembly in the interior of the handle.

In an alternative embodiment, the handpiece includes an electrical connection constituted by a chain of component parts for the mechanical transmission of rotational movement, to assure the transmission of appropriate movement, and for the conduction of electrical energy from a connection provided at the extremity of the handle (for interacting with an external motor) and as far as the instrument. In one variant, the electrical connection is constituted by a conducting wire. In another variant, the electrical connection is an elastic connection component for providing an electrical connection between the component parts of the mechanical transmission and the head of the tool.

In another alternative embodiment, the head contains a turbine, and the body of the handpiece includes fluid channels that are necessary for its function.

The interior housing of the head is preferably adapted to receive a tool-holder assembly comprised of mechanical transmission component parts of the head, and to receive a means for tightening and releasing the tool or the instrument. The housing opens out onto the head via an opening that is closable by a stopper or a cap, or by a push-button.

The handpiece preferably comprises an arrangement for the attachment of a dental instrument to the tool-holder assembly, for the attachment and rotational driving of a dental tool or instrument about a driving axis. The tool-holder assembly is integrated into the head of the dental handpiece, and is connected to a transmission assembly integrated in the handle of the handpiece, and is principally comprised of a deformable and elastic tightening and releasing means in the form of a belt. At least one part of the belt has a section adapted for engagement in a groove or an annular slot provided in the upper part of the instrument, and is adapted to retain the instrument by tightening on the instrument. The tightening and releasing means also includes means for the application of releasing forces for canceling such tightening forces, for the purpose of releasing the instrument. The foregoing attachment arrangement is preferably detachable from the tool-holder.

In one variant, the belt is made of a deformable, elastic material, and exhibits a form that is essentially that of a parallelogram having a central zone which is provided for the purpose of retaining the head of the instrument tightly in place at the level of a slot. In another variant, the elastic, deformable belt exhibits the form of a split ring or a split annular clip including an annular shoulder adapted for engagement in an annular slot in the instrument, and a conical part for interacting with a complementary conical part of a push-button.

Depending upon the embodiment employed and/or the operating speed of the tool, the attachment arrangement can include a push-button. The push-button may or may not be integral with the tool-holder, and can be retained in an opening in the head, for example, by clipping.

Further description of the present invention is provided below, with reference to the following drawings.

BRIEF DESCRIPTION OF THE DRAWINGS

FIG. 1 is an isometric view of a handpiece produced in accordance with the present invention.

FIG. 2 is a longitudinal section of the handpiece shown in FIG. 1.

FIG. 4 is an isometric view of a partial section of another embodiment of the present invention, having a tightening and releasing means in the form of a lozenge-shaped elastic belt which is capable of being released manually.

FIG. 5 is a view of an axial section of the view shown in FIG. 4.

FIG. 6 is a partial transverse section of the head shown in FIG. 4, illustrated at the level of the elastic belt.

FIG. 9 is an isometric view, shown in partial section, of the embodiment shown in FIG. 8.

FIG. 10 is an isometric view of the elastic belt shown in FIGS. 8 and 9.

FIG. 11 is an axial section of another embodiment of the present invention, having a tightening and releasing means in the form of a split ring.

FIGS. 12 and 13 are isometric views of the push-button shown in FIG. 11.

DETAILED DESCRIPTION OF PREFERRED EMBODIMENTS

General Concept of the Body of the Handpiece

Figure 3:
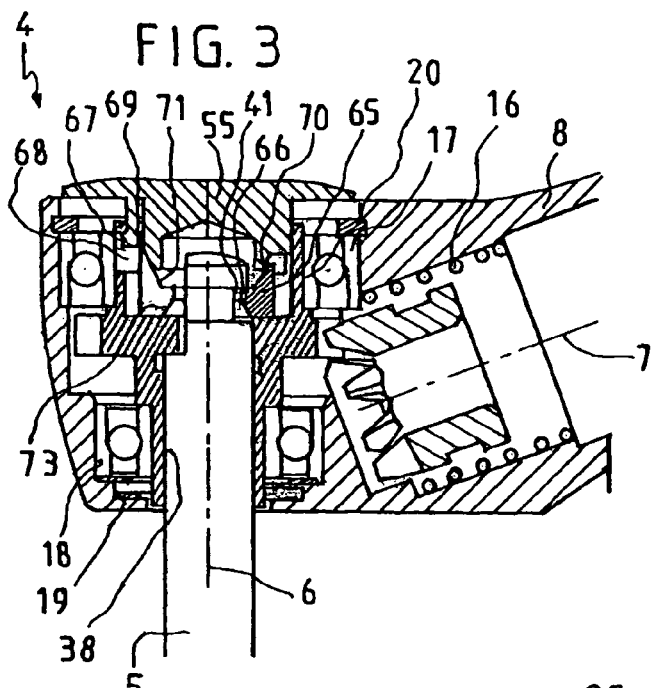
FIG. 3 is a partial longitudinal section of an embodiment of the present invention.
Figure 14:
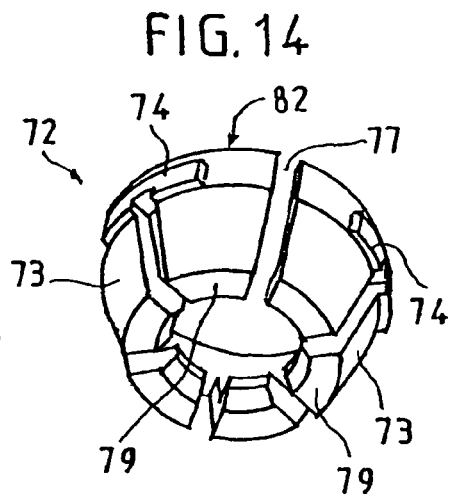
FIGS. 14 and 15 are isometric views of a tightening and releasing means in the form of a split annular clip, as shown in FIG. 11.

Reference is first made to the non-restrictive examples of the present invention shown in FIGS. 1 to 3.

In this embodiment, a handpiece (1) includes a body (2) formed as a single piece. One part of the body (2) serves as a handle (3) having a rectilinear axis, and another part of the body (2) constitutes a head (4) for the attachment and driving of an instrument (5) about a driving axis (6). The driving axis (6) is capable of being aligned with the axis (7) of the handle, or is capable of forming a predetermined angle with the axis (7) of the handle which lies between 90 and 180°, and preferably between 100 and 130°, as illustrated in the non-restrictive examples shown in the various figures.

The body is formed by an envelope (8), or external casing. The envelope (8) can be formed in a single piece, or in multiple pieces, and can be electrically insulating. The envelope (8) can, for example, be produced in a polymeric, thermoplastic or thermosetting material (preferably polyetherether ketone, abbreviated to PEEK in the text which follows), and incorporates the mechanical component parts of the handle and the head, together with electrical connection means. This then ensures transmission of the movement and the electrical energy from a connection (9) provided at the extremity of the handle, for interacting with an external motor (not shown), as far as the instrument (5) secured in the head (4).

The contra-angle handpiece (1) shown in FIGS. 1 to 3 exhibits two axes (6) and (7). This leads to the potential for friction inherent in each bearing to be limited in order to guarantee the most stable possible output. For this reason, ball bearings are in this case also integrated in the envelope (8). Such an arrangement of the contra-angle handpiece lends itself particularly well to root canal treatments (endodonty) with an apex locator.

The handpiece of the present invention, when connected and coupled to a motor, may thus, for example, produce a rotational movement in an instrument (5) (a root canal instrument, for example), as well as convey an electric current that is capable of being utilized for the detection of the apex. The electrical connection between the motor and the handpiece (see FIGS. 2 and 3) can be effected by any connection, for example, between an attachment hook for the motor and an attachment groove (10) of a socket (11) (or by means of a telescopic button, for example). The envelope (8), which is insulating, is held by the practitioner in his hand, and the extremity at the head (4) is placed in the patient's mouth.

In the configuration shown, the chain of mechanical transmission and electrical component parts is constituted as follows. Inside the handle, electrical current passes from the socket (11) to a fixed external race of a first bearing (12), then to a first spring (13), then to a fixed external race of a second bearing (14), then to a ring (15) that is retained axially on a first shoulder in the envelope (8), and then to a spring (16) that is retained axially by a second shoulder of the envelope (8).

The first and second bearings (12, 14) support a transmission shaft along the longitudinal axis (7) of the handle, or the first axis of the handpiece (1). The springs (13, 16) are compression springs having coils that are arranged externally to the transmission shaft (7). At this stage, the electrical current has crossed the handle of the contra-angle, or the handpiece (1).

As an alternative, a conducting wire can run from the extremity of the handpiece (1) which communicates with the motor to the contact with the instrument or tool (5).

The head (4) of the contra-angle handpiece, with its second axis or drive axis (6), supports two ball bearings (with oblique contact, if possible), namely an upper bearing (17) and a lower bearing (18). The external race of the upper bearing (17) interacts with the second spring (16) of the handle. Axial play in the lower bearing (18) is taken up with an elastic washer (19). In this type of bearing assembly, the balls of the bearings are in contact at all times with the external and internal races of the bearings, thereby ensuring an electrical connection between fixed parts and moving parts.

A barrel pinion (20) is mounted on the drive shaft (6) and includes teeth (21) engaging with the teeth (22) of an output pinion (23) of the handle. The barrel pinion (20) is conductive and integral with the interior races of the bearings, and ensures the conduction of electricity to the instrument (5), as well as mechanically driving the instrument (5). The electrical current that is conveyed to the extremity of the instrument will delimit the apex through the effect of variation in the resistance, taking into account the external insulation of the envelope (8), and a push-button (55) provided on the head (4) which will be described in greater detail below.

As a variant, the electrical connection between the second bearing (14) and the head (40) of the instrument is provided by an elastic and electrically conducting connecting component (88). The mechanical drive for the instrument is again provided by the barrel pinion (20), as previously described. The connecting component (88) can be a strip, for example, or a bar of circular or rectangular section. A first peripheral segment (89) of the connecting component (88) is engaged in a slot (90) formed in the race (15) of the bearing (14). A second peripheral segment (91) of the connecting component (88), at the opposite end of the first segment, is supported against the head (40) of the instrument. The slot (90) maintains the connecting component perpendicular to the axis of the instrument when the push-button is not activated.

Use of the connecting component (88) is particularly advantageous because, on the one hand, the support on the push-button (55) has a tendency to repel the head (40) of the instrument and because, on the other hand, contact by the connecting component with the head (40) is centered on the axis of the instrument due to the spherical surface of the head, resulting in a rate of friction which is close to zero.

Concept of the Attachment Arrangement and the Means of Tightening and Releasing of the Instrument in the Head The following are preferred, and non-limiting embodiments of means for attaching an instrument in the head (4) and for tightening and releasing the instrument.

In the course of root canal treatment, for example, accessibility of the molars must be guaranteed for comfort and quality, both for the practitioner and for the patient. For this reason, the head of the tool-holder assembly (24) of the present invention is comprised of mechanical transmission component parts that are as small and compact as possible. This is achieved with a novel, compact tightening and releasing means (25), which is not bulky and which is part of the attachment assembly.

The tightening and releasing means (25) includes a deformable and elastic belt (25) which can be made of a plastic material (PEEK, for example), and which is itself capable of assuring the functions of tightening and releasing. Releasing is performed by centripetal manual action on the belt, and tightening is performed by relaxing this action. An internal housing (26) in the head is adapted to receive the tool-holder assembly (24) and the tightening and releasing means (25). The internal housing (26) opens out onto the head via an opening (27) that is capable of being closed by a stopper or a cap (28), or by a push-button. Such a solution will be appreciated more fully from the description of the following two embodiments.

A first alternative embodiment is described in conjunction with FIGS. 4 to 7. Releasing is, in this embodiment, controlled by a direct manual action on the belt. The housing (26) of the tool-holder assembly (24) includes a lower, cylindrical part (29) that is coaxial with the driving axis (6) and which has a diameter adapted to receive the barrel (30) of the barrel pinion (20). An upper, essentially cylindrical part (31), is similarly coaxial with the driving axis (6) and has a larger diameter. The cylindrical part (31) is provided to receive the teeth (21) of the pinion barrel, with its means for interlocking the instrument, as well as a tightening and releasing device which is described below.

The discharge opening (27) of the upper part of the housing (31) is closed by a stopper or cap (28) which is preferably, although not necessarily made of the same material as the envelope (8). The upper part of the housing (31) similarly has a lateral opening (32) that discharges into an internal housing (33) of the handle (3), to permit the engagement of the teeth of the barrel pinion (20) with the teeth of the output pinion (23) of the handle (3).

The barrel pinion rotates freely in the head, and its axial standard is assured between, on the one hand, the base (34) of the upper part of the housing, which forms a shoulder, and on the other hand, the frontal surface (35) of the stopper. The resulting axial freedom of the barrel pinion is on the order of a few hundred parts of a millimeter. Rotational movement of the output pinion (23) is transmitted to the barrel pinion (20), and then to the instrument (5), by a plane surface (36) which is provided on the instrument and interaction with a plane surface (37) provided in the internal bore (38) of the barrel pinion.

For the embodiment of FIGS. 4 to 7, the tightening and releasing means is essentially a belt (25) made of a deformable and elastic material which essentially exhibits the form of a lozenge having a central zone (39). The central zone (39) is provided to retain the head (40) of the instrument securely in place at the level of an annular blocking slot (41) provided at the upper extremity of the instrument. The large diagonal of the lozenge is provided to ensure that its two extremities extend diametrically beyond the envelope of the head (4), as two projections (42), each located in a notch (43) in the head. The notch (43), on the one hand, discharges into the upper part (31) of the housing and, on the other hand, discharges into the opening (27) receiving the stopper.

A direct, centripetal, manual action on the two projections (42) simultaneously brings about the release of the instrument, and the relaxation of this action assures the tightening of the instrument. The flanges (44) of the notches (43) ensure blocking against rotation of the belt, which is centered in the head by detachments (45) provided in proximity to the projections (42) and supported on the periphery (46) of the upper part of the housing (26).

The axial standard of the belt is assured, on the one hand, by a shoulder (47) provided in the base (48) of an axial cavity (49) of the stopper, for accommodating the head (40) of the instrument, and on the other hand, by the base (50) of the notches. In this way, the belt does not touch the rotating part of the barrel pinion.

In the free state, the belt interacts with an upper shoulder (51) of the annular slot of the head of the instrument in order to bring about a first axial limitation of the instrument. A second axial limitation of the instrument is assured by a plane surface (52) on the barrel pinion, which interacts with a transverse extremity (53) of the plane surface of the instrument.

Unlocking of the instrument involves the application of two diametrically opposed pressing forces to the projections (42), which forces are directed toward the axis of rotation. These two forces give rise to an orthogonal component, thereby releasing the instrument. The act of simultaneously and directly pressing on the two ears of the belt (with the thumb and index finger, for example) guarantees tightening at the mouth, as compared with a push-button system, for example. Attachment of the instrument can be effected without applying pressure to the two ears of the belt due to a conical part (64) which is provided on the undersurface of the central zone (39) in the belt, in conjunction with axial displacement of the instrument which causes a radial displacement of the belt, by elasticity. The belt then resumes its form to assure the tightening function.

Figure 8:
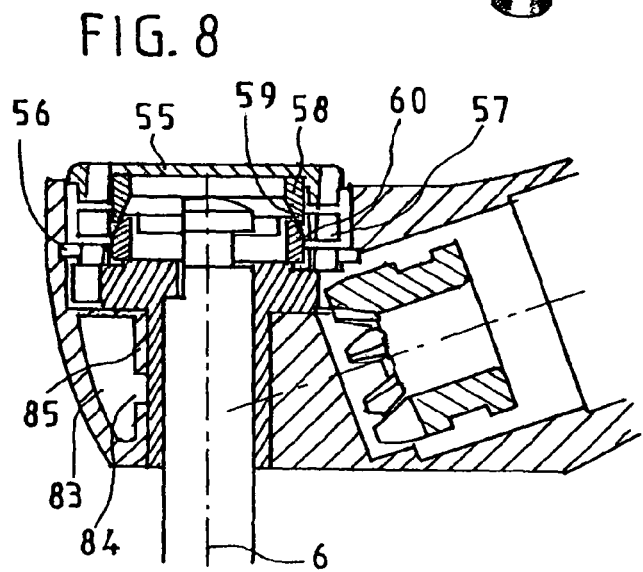
FIG. 8 is an axial section of another embodiment of the present invention, having a tightening and releasing means in the form of an elastic belt capable of being released by the actuation of a push-button.

A second alternative embodiment of the tightening and releasing means is described in conjunction with FIGS. 8 to 10.

The elastic belt (25), which has the form of a lozenge and a central zone (39) for the purpose of securing the instrument, differs from the previously described belt in that its ears (54) form projections perpendicular to the plane of the belt and are situated on the same side of the plane of the belt, and because the belt is maintained in position axially and radially by the barrel pinion, as illustrated in FIGS. 8 and 9. To this end, the two extremities of the belt cross two peripheral gaps (61) provided on the upper flange (62) of the barrel pinion, which are diametrically opposed and arranged on a plane transverse to the driving axis (6), and the two ears (54) are blocked against rotation by two notches (63) on the flange. Furthermore, the head is distinguished from the previously described head in that the stopper is replaced by a push-button (55). The push-button (55) has a metallic insert, for example, to facilitate its manufacture.

In this embodiment, the push-button (made of PEEK for example) includes a plurality of component parts. An elastic ring (56) is provided at the lower extremity which restricts the axial freedom of the barrel pinion and retains the push-button on the head (4). An intermediate elastic zone (57) is provided which plays the role of a return spring for the push-button. An internal cylindrical insert (58) is provided which, when the push-button is pressed, permits the deformation of the elastic belt to be controlled, thereby releasing the tool. For this purpose, pressing on the push-button (55) compresses its spring (57), causing the internal conical form (59) of the insert (58) to interact with the complementary conical flanges (60) of the ears of the belt. The resulting radial component on the ears (54) of the belt induces another radial deformation perpendicular to the primary radial component which permits unlocking of the instrument.

Introduction of the instrument into the head can be effected by pressing on the push-button, or without pressing on the push-button. In the latter case, a conical arrangement (64) on the undersurface of the central zone (39) of the belt permits the introduction of the instrument. The configuration of the belt contributes to being able to guarantee tightening, through a centrifugal effect during rotation.

Concept of Push-Buttons

Miniaturization is constantly sought in the field of medical equipment, such as the heads of contra-angle handpieces used in dentistry. New materials, such as thermoplastic or thermosetting polymer materials, help meet this need. Previously known mechanisms can be reconsidered by taking into account the mechanical, physical and chemical characteristics of these new materials and, at the same time, by reducing the number of component parts. Improvements in quality and reductions in cost of the assembly are possible because the plastic parts can be machined or injection molded. In addition to miniaturization, such plastic materials also afford lightness, the ability to slide when used with dynamic equipment, high resistance to sterilization or disinfection, and favorable elastic characteristics. For these reasons, such plastic materials can be utilized in the production of dental handpieces.

The control for tightening or releasing of the tool generally takes the form of the manual actuation of the push-button on the head of the handpiece. The push-button can be integral with the dynamic assembly (rotating, vibrating, etc.), for example, for endodonty, and can be a fixed push-button independent of the dynamic assembly.

A head of a handpiece having a drill handle in place has previously been illustrated, as an example of one application of the improvements of the present invention, with reference to FIGS. 2 and 3.

Figure 7:
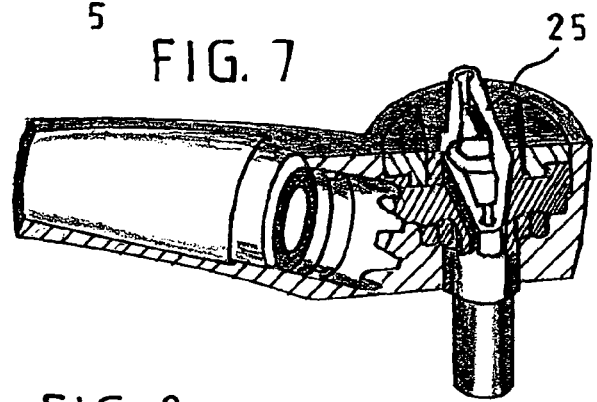
FIG. 7 is an isometric view, shown in partial section, of the head shown in FIG. 4.
Figure 15:
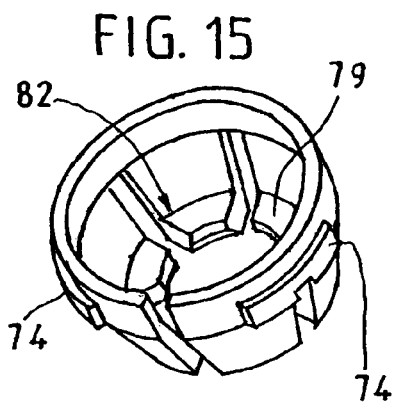

It is again pointed out that the body of the head (4), whether or not unitary with the handle (3), is fitted with a rotating barrel pinion (20) that is caused to rotate by an output pinion (23) in the handle. The barrel pinion possesses a freedom of rotation and an axial connection that are assured, for example, by ball bearings. It is, of course, possible to implement solutions which do not use ball bearings, as illustrated in FIGS. 5 and 7, having inserted slide bearings or having slide bearings molded into the body of the head.

The transmission of rotational movement for the drill handle is assured by the cooperation of the plane surface (36) provided on the barrel pinion (20) and the plane surface (37) of the tool. The axial standard of the tool is guaranteed by the shoulder on the plane surface of the barrel pinion and by the shoulder on the complementary plane surface of the tool.

For the various alternative embodiments previously described, it is possible to distinguish between two types of push-buttons that are useful in accordance with the present invention.

A Push-Button Integral with the Dynamic Assembly

Figure 16:
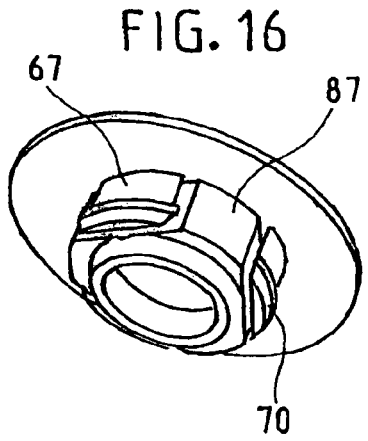
FIG. 16 is an isometric view of a push-button, as shown in FIG. 3.
Figure 17:
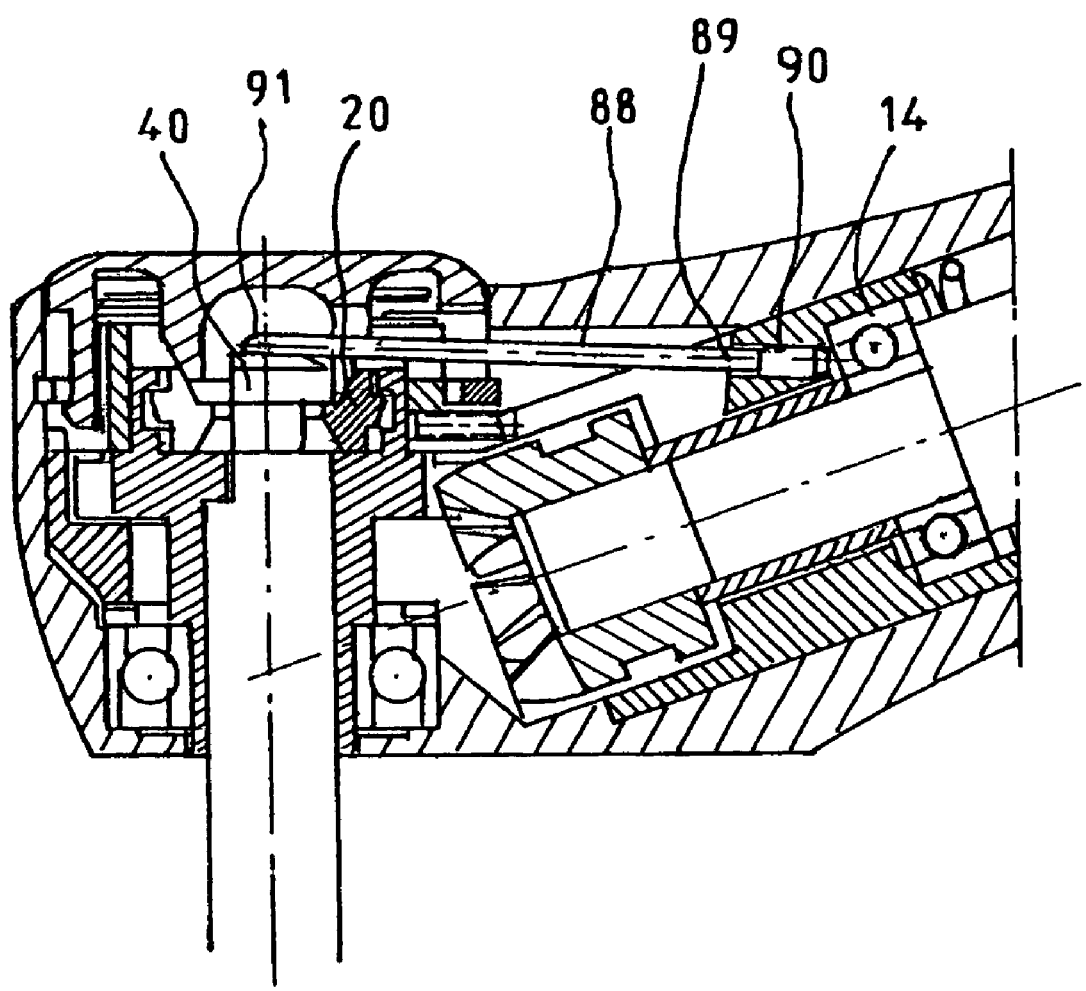
FIG. 17 is a sectional view of an alternative of the embodiment shown in FIG. 3, having an elastic and conducting connecting component part.

Such a push-button, known as a tool-holder, is illustrated in FIGS. 3 and 16 by the reference number (55), and is characterized by permanent contact between a rotating locking assembly and the push-button. In the state of rest, the push-button (55) (made from PEEK, for example) provides an axial limit for an elastic split ring (65) (also made from PEEK, for example) and, at the same time, centers the ring (65) in relation to the axis (6). The ring (65) has an externally cylindrical form, and an internal wall that includes an upper flange with a conical gradient (71) and an intermediate part in the form of a transverse shoulder (66) directed toward the axis (6). The shoulder (66) of the ring (65) retains the instrument (5) in the axial direction by engaging the annular slot (41). The push-button (55) is guided radially in the bore (38) of the barrel pinion by one or more sectors or components (87) arranged on the undersurface of the push-button (55), each terminated by a conical extremity for the purpose of pressing on the elastic ring (65).

Axial displacement of the push-button (55) is limited between the upper and lower extremities of one or more gaps (68) made in the upper body of the barrel pinion. One or more hooks (67) provided on the undersurface of the push-button can interact with the gaps (68). The ring (65) applies an axial component to the push-button (55) to return it to its initial position. Due to their radial elasticity, and due to slots (69) provided between the hooks and the sectors (87), the hooks (67) permit a "clipping" engagement of the push-button in the barrel. Pressing on the push-button (55) permits unlocking of the tool (5) by means of the conical parts (70) which engage the complementary conical gradient (71) of the elastic ring in order to disengage the shoulder (66). Introduction of the instrument (5) into the barrel pinion can take place automatically, without the need to press on the push-button, due to the conical part (73) provided on the undersurface of the elastic ring at the extremity of the shoulder (66). In FIG. 3, the tightening and releasing means is a split elastic ring that is open along a radial plane visible on the sectional plane shown in FIG. 3, and the means for applying the releasing forces are constituted by the conical gradient (71).

A Push-Button Independent of the Dynamic Assembly

For applications in which the tool is held in the practitioner's hand, the push-button and the locking means are generally separated. One such embodiment is illustrated by way of example in FIGS. 11 to 15.

In the state of rest, and whether or not in dynamic assembly, without actuation of the push-button, a conical, elastic annular clip (72) axially retains the tool (5) via arms (73) (for example, 6 arms), each of which is terminated by a shoulder (79) directed toward the axis (6). The clip (72) is integral with the rotating barrel pinion due to the engagement of peripheral projections (74) of the clip in corresponding openings (76) made in the barrel pinion. A slot (77) completely traverses the clips to permit the assembly and disassembly of the clip in the bore of the barrel pinion, thereby imparting the necessary radial elasticity.

The push-button (55) is retained axially and is centered by elastic blades (75) cut into the cap of the push-button, in the opening (27) in the head. The blades, when assembled under tension in the body of the head, offer an elastic axial freedom along the axis (6) of the push-button. FIGS. 12 and 13 illustrate the blades (75) in a constrained position and show clipping grooves (80) at the end of the blades for clipping the push-button (55) into the opening (27). A manual, axial pressing on the push-button is translated into an axial displacement of the conical base (78) of the push-button, which then interacts with the complementary cone (82) of the internal conical cavity of the arms (73) of the clip. Release of the tool is then assured by separation of the arms (73) and disengagement of the shoulders (79). When manual pressure on the push-button is released, the respective cones of the two component parts (55) and (72) are no longer in contact, and the push-button resumes its initial position.

In the embodiment of FIGS. 11 to 15, the tightening and releasing means is the elastic, conical clip (72), the shoulders (79) of which are adapted to engage in the groove or annular slot (28) of the instrument. The means for applying the releasing forces is constituted by the conical internal form (82) of the clip (72), the radial deformation of which is ensured by the slot (77).

Concept of Greasing

With reference to FIG. 8, which is an axial section through FIG. 9, the head includes a cavity (83) which is provided around, or to the side, of the barrel of the barrel pinion for the purpose of containing a solid grease. The solid grease is released in a small quantity on each use in order to lubricate the barrel. The solid grease is released from the separating wall (85) between the cavity and the barrel via an orifice (84).

Assembly Concept

The envelope (8) can be produced in a single piece by molding a plastic material (for example PEEK) having electrically insulating properties, or a fritted material containing metallic inclusions (for example Metal Injection Molding, abbreviated to M.I.M.) having electrically conducting properties, or any other material. The head of the envelope includes a first housing (26) for the attachment of a tool-holder and an instrument along the drive axis (6). The housing (26) opens out to either side of the head via two openings. At least one of the openings, the opening (27), exhibits dimensions which permit the introduction of all of the component parts of the head, as well as their assembly, inside the head. A second housing (33), having a rectilinear axis (7), on the one hand opens out at the distal extremity of the handle via an opening (81), and on the other hand opens out at the proximal extremity of the head. The second housing (33) opens into the first housing (26) via a lateral opening (32), permitting interaction between the mechanical components of the head and those of the handle. In addition, the opening (81) is dimensioned to permit the introduction of all of the components of the handle, as well as their assembly in the interior of the second housing (33), along a rectilinear axis (referred to herein as the axis (7) of the handle).

To produce a contra-angle handpiece, an envelope is provided in which the axes (6) and (7) form, for example, an angle of between 90 and 180°, and preferably between 100 and 130°. To produce a straight handpiece, the axes (6) and (7) must be parallel and displaced from one another to provide an opening in the head (27) for the assembly of the internal component parts, and for fitting the stopper of a push-button.

The foregoing assembly concept is particularly advantageous because it provides the possibility of reducing the number of bearings, or completely eliminating the bearings, reducing the cost of the handpiece, reducing the dimensions of the handpiece, facilitating cleaning (smooth contours) and improving hygiene (a single piece, and no interface).

The invention claimed is:

1. A dental handpiece including mechanical components and comprising a tool-holder assembly for attaching and for rotationally driving a dental instrument about a drive axis, and an assembly for transmitting rotational movement to the tool-holder assembly;
wherein the mechanical components are mounted in interior portions of a body having a head and a handle, wherein the body is formed as a unitary, electrically insulating envelope including one part which serves as the handle and another part which constitutes the head;
wherein the head includes a first housing having at least one opening dimensioned to permit component parts of the head to be introduced into and assembled within interior portions of the first housing;
wherein the handle includes a second, longitudinal housing having a longitudinal axis, and an opening at an end of the handle opposite to the head which is dimensioned to permit internal component parts of the handle to be introduced into and assembled within interior portions of the second housing, and a lateral opening communicating with the first housing;
wherein electrical current is conducted from a casing associated with the end of the handle opposite to the head, for connection to a drive motor, to the lateral opening communicating with the first housing by internal component parts of the handle; and
wherein the head includes a barrel pinion assembled for rotation about the drive axis, wherein the barrel pinion includes teeth operatively coupled with teeth of an output pinion associated with the internal component parts of the handle, and wherein the barrel pinion is electrically conductive and ensures an electrical connection between the internal component parts of the handle and the dental instrument coupled with the tool-holder assembly.

2. The dental handpiece of claim 1 wherein the electrical current is conducted from the end of the handle opposite to the head to the lateral opening communicating with the first housing by an electrical connection comprised of a chain of component parts for the mechanical transmission of rotational movement to the tool-holder assembly.

3. The dental handpiece of claim 2 wherein the chain of component parts is located inside the handle and include a socket coupled with the end of the handle opposite to the head, a fixed external race of a first bearing coupled with the socket, a first spring having a first end coupled with the external race of the first bearing and a second, opposite end coupled with a fixed external race of a second bearing, a ring coupled with the external race of the second bearing and retained axially on a first shoulder of the envelope, and a second spring coupled with the ring and axially retained by a second shoulder of the envelope.

4. The dental handpiece of claim 3 wherein the first bearing and the second bearing support a transmission shaft along the longitudinal axis of the handle, and wherein the first spring and the second spring are compression springs having coils external to the transmission shaft.

5. The dental handpiece of claim 3 wherein the head supports two ball bearings having axes aligned with the drive axis, including an upper bearing having an external race coupled with the second spring of the handle and a lower bearing having an elastic washer for taking up axial play in the bearings, wherein the barrel pinion is mounted on a drive shaft, and wherein the barrel pinion is integral with interior races of the two ball bearings, for conducting electricity to and rotationally driving the dental instrument.

6. The dental handpiece of claim 5 wherein the electrical current is conducted from the end of the handle opposite to the head to the dental instrument by the chain of component parts.

7. The dental handpiece of claim 3 wherein the electrical current is conducted from the internal component parts of the handle to the component parts of the head by an elastic connection device.

8. The dental handpiece of claim 7 wherein the elastic connection device includes a first peripheral segment engaged in a groove formed in the race of the second bearing, and a second peripheral segment, opposite to the first peripheral segment, which is supported against head portions of the dental instrument.

9. The dental handpiece of claim 1 wherein the electrical current is conducted from the end of the handle opposite to the head to the lateral opening communicating with the first housing by an electrical connection comprised of a conducting wire.

10. The dental handpiece of claim 1 wherein the first housing receives the tool-holder assembly, and means for tightening and releasing the dental instrument.

11. The dental handpiece of claim 1 wherein the head includes a cavity for containing a solid grease that is released on each use from a separating wall between the cavity and the barrel pinion, through an orifice, for lubricating the barrel pinion.

12. The dental handpiece of claim 1 which further includes an attachment for connecting a dental instrument to the tool-holder assembly, wherein the attachment includes a deformable and elastic belt for tightening upon and releasing the dental instrument, wherein at least one part of the belt has a section for engaging an aperture provided in upper portions of the dental instrument, and means for applying releasing forces for releasing the instrument.

13. The dental handpiece of claim 12 wherein the attachment is detachably associated with the tool-holder assembly.

14. The dental handpiece of claim 12 wherein the belt forms a parallelogram having a central zone for retaining a head of the dental instrument in place at the level of the aperture, wherein the parallelogram has a large diagonal including two extremities extending diametrically beyond an envelope defined by the head as two projections, wherein each of the projections is located in a notch in the head, and wherein the projections form means for manually and directly applying forces for releasing the belt.

15. The dental handpiece of claim 14 wherein the belt includes detachments in proximity to the projections, and wherein the detachments rest on peripheral portions of the housing of the head.

16. The dental handpiece of claim 14 wherein the belt further includes a conical part located on an undersurface of the central zone.

17. The dental handpiece of claim 14 wherein the belt further includes two ears forming projections perpendicular to a plane defined by the belt and situated on the same side of the defined plane, and wherein the ears apply tightening forces in cooperation with the barrel pinion.

18. The dental handpiece of claim 17 wherein the ears include conical flanges.

19. The dental handpiece of claim 17 wherein the attachment further includes a push-button having an elastic ring at a lower extremity, for retaining the push-button on the head, an intermediate elastic zone which operates as a return spring for the push-button, and an internal cylindrical insert for deforming the belt and for releasing the tool when the push-button is pressed.

20. The dental handpiece of claim 19 wherein the cylindrical insert has an internal conical form for interacting with complementary conical flanges on the ears of the belt.

21. The dental handpiece of claim 12 wherein the belt has a split structure including an annular shoulder for engaging an annular slot in the dental instrument, and a conical part for interacting with a complementary conical part of a push-button.

22. The dental handpiece of claim 21 wherein the split structure is a split ring including a conical part provided on in undersurface of the split ring for receiving the dental instrument.

23. The dental handpiece of claim 22 wherein the push-button is axially guided by at least one sector arranged on the undersurface and terminated by a conical extremity.

24. The dental handpiece of claim 22 wherein the push-button has elastic blades cut into a cap of the push-button and terminated by clipping slots and a conical base.

25. The dental handpiece of claim 12 wherein the attachment further includes a push-button for applying releasing forces on means for tightening and releasing of the dental instrument.

26. The dental handpiece of claim 25 wherein the push-button is integral with the tool-holder assembly.

27. The dental handpiece of claim 25 wherein the push-button is retained by a clip located in an opening in the head.

28. The dental handpiece of claim 1 wherein the drive axis of the head and the longitudinal axis of the handle form an angle for producing a contra-angle handpiece.

29. The dental handpiece of claim 28 wherein the angle is between 100° and 130°.

30. The dental handpiece of claim 1 wherein the envelope is a molded part.

31. The dental handpiece of claim 30 wherein the envelope is formed of a polymer material.

32. The dental handpiece of claim 31 wherein the polymer material is PEEK.

\* \* \* \* \*